United States Patent [19]

Guentner et al.

[11] Patent Number: 4,841,050

[45] Date of Patent: Jun. 20, 1989

[54] CARBAZOLE CONTAINING BENZOPYRANS

[75] Inventors: Andreas Guentner; Udo Mayer, both of Frankenthal; Andreas Oberlinner, Ludwigshafen, all of Fed. Rep. of Germany

[73] Assignee: BASF Aktiengesellschaft, Ludwigshafen, Fed. Rep. of Germany

[21] Appl. No.: 25,063

[22] Filed: Mar. 12, 1987

[30] Foreign Application Priority Data

Mar. 12, 1986 [DE] Fed. Rep. of Germany ....... 3608215

[51] Int. Cl.$^4$ ................. C07D 405/06; C07D 413/14
[52] U.S. Cl. .................................. 544/150; 544/151; 546/196; 548/439; 548/444
[58] Field of Search ............... 544/150, 151; 546/196; 548/439, 444

[56] References Cited

U.S. PATENT DOCUMENTS 3,909,260 9/1975 Seoka et al. .................... 548/444

Primary Examiner—Robert W. Ramsuer
Attorney, Agent, or Firm—Oblon, Spivak, McClelland, Maier & Neustadt

[57] ABSTRACT

Benzopyrans of the formula

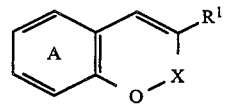

where X is a radical

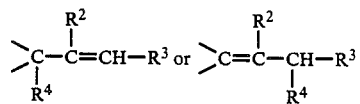

and $R^1$, $R^2$, $R^3$, $R^4$ and the ring A have the meanings stated in the description, a process for their preparation, and their use in pressure-sensitive or heat-sensitive layers.

1 Claim, No Drawings

CARBAZOLE CONTAINING BENZOPYRANS

The present invention relates to novel benzopyrans which have a side chain in ring position 2, a process for their preparation and their use in pressure-sensitive or heat-sensitive recording systems.

We have found benzopyrans of the general formula I

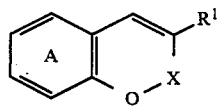

where $R^1$ is unsubstituted or substituted $C_1-C_8$-alkyl, unsubstituted or substituted phenyl, $C_1-C_5$-alkoxy or halogen, X is a radical

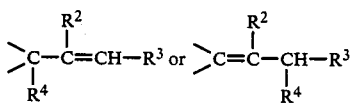

$R^2$ is hydrogen or, together with $R^1$, is $C_2$- or $C_3$-alkylene which is unsubstituted or substituted by $C_1-C_4$-alkyl, $R^3$ is phenyl which is unsubstituted or substituted by $C_1-C_4$-alkyl (which in turn may be substituted by phenyl), cyclohexyl, halogen, $C_1-C_8$-alkoxy, $C_1-C_8$-mono- or dialkylamino (each of which in turn may be substituted by phenyl or chlorine), phenylamino (which in turn may be substituted by $C_1-C_8$-alkyl on the phenyl ring or on the nitrogen atom), pyrrolidino, piperidino or morpholino, and which furthermore may be substituted by $C_1-C_5$-alkyl, $C_1-C_5$-alkoxycarbonyl, $C_1-C_5$-dialkylaminocarbonyl, pyrrolidinocarbonyl, piperidinocarbonyl, morpholinocarbonyl, $C_1-C_8$-alkoxy or halogen; or is naphthyl which is unsubstituted or substituted by $C_1-C_4$-alkoxy; or is carbazol-3-yl or 1,2,3,4,4a,9a-hexahydrocarbazol-6yl, each of which may be substituted on the nitrogen atom by $C_1-C_5$-alkyl or benzyl, or is indol-3-yl, which may be substituted in ring position 1 and/or 2 by unsubstituted or phenyl-substituted $C_1-C_5$-alkyl; or is thiazol-5-yl which is substituted in ring position 2 by unsubstituted or phenyl-substituted $C_1-C_5$-mono- or dialkylamino, pyrrolidino, piperidino or morpholino and may be substituted in ring position 4 by $C_1-C_5$-alkyl, phenyl or chlorine, and $R^4$ is hydroxyl, $C_1-C_5$-alkoxy, unsubstituted or substituted phenoxy, unsubstituted or substituted phenylsulfonyl, pyrrolidino, piperidino, morpholino or a radical of a CH-acidic compound, and the ring A may be fused to a benzo ring, may be substituted by $C_1-C_4$-alkyl, chlorine or bromine, or may be substituted in ring position 7 by $C_1-C_5$-mono- or dialkylamino (each of which in turn may be substituted by chlorine or phenyl), pyrrolidino, piperidino, morpholino, hydroxyl or $C_1-C_4$-alkoxy.

All alkyl groups occurring in the abovementioned radicals may be either straight-chain or branched.

In formula I, $R^1$ is, for example, methyl, ethyl, propyl, isopropyl, butyl, isobutyl, tert-butyl, pentyl, isoamyl, hexyl, heptyl, octyl, 2-ethylhexyl, phenyl which is unsubstituted or substituted by $C_1-C_4$-alkyl, $C_1-C_4$-alkoxy or halogen, such as 4-methylphenyl, 2-methylphenyl, 4-ethylphenyl, 4-isopropylphenyl, 4-methoxyphenyl, 2-ethoxyphenyl, 4-chlorophenyl or 2,4-dichlorophenyl, methoxy, ethoxy, propoxy, isopropoxy, butoxy, fluorine, chlorine or bromine.

In formula I, $R^2$ is, for example, hydrogen or, together with $R^1$, is 1,2-ethylene, 1,2-propylene or 1,3-propylene.

In formula I, $R^3$ is, for example, phenyl or, preferably, phenyl which is substituted in ring position 4 by methyl, ethyl, propyl, isopropyl, butyl, sec-butyl, benzyl, 2-phenylethyl, cyclohexyl, fluorine, chlorine, bromine, methoxy, ethoxy, propoxy, isopropoxy, butoxy, pentyloxy, hexyloxy, 2-ethylhexyloxy, methylamino, ethylamino, isopropylamino, butylamino, 2-ethylhexylamino, benzylamino, 2-chloroethylamino, dimethylamino, diethylamino, dibutylamino, methylethylamino, di(2-ethylhexyl)-amino, anilino, 4-methylanilino, 4-ethylanilino, N-methylanilino, N-ethylanilino, pyrrolidino, piperidino or morpholino; or is, for example, 2,4-dimethylphenyl, 2-methoxycarbonyl-4-dimethylaminophenyl, 2-ethoxycarbonyl-4-dimethylaminophenyl, 2-dimethylaminocarbonyl-4-methoxyphenyl, 2-pyrrolidinocarbonyl-4-methylphenyl, 2-piperidinocarbonyl-4-dimethylaminophenyl, 2-morpholinocarbonyl-4-methylphenyl, 2,4-dimethoxyphenyl, 3,4-dimethoxyphenyl, 2-methoxy-4-dimethylaminophenyl, 2-methoxy-4-dibenzylaminophenyl, 2,4-dichlorophenyl, naphthyl, 4-methoxynaphthyl, carbazol-3-yl, N-methylcarbazol-3-yl, N-ethylcarbazol-3-yl, N-benzylcarbazol-3-yl, 1,2,3,4,4a,9a-hexahydrocarbazol-6-yl, N-methyl-1,2,3,4,4a,9a-hexahydrocarbazol-6-yl, N-ethyl-1,2,3,4,4a,9a-hexahydrocarbazol-6-yl, N-benzyl-1,2,3,4,4a,9a-hexahydrocarbazol-6-yl, indol-3-yl, 1-methylindol-3-yl, 1-ethylindol-3-yl, 1-benzylindol-3-yl, 1(2-phenylethyl)indol-3-yl, 2-methylindol-3-yl, 1,2-dimethylindol-3-yl, 1-benzyl-2-methylindol-3-yl, 2-methylaminothiazol-5-yl, 2-dimethylaminothiazol-5-yl, 2-diethylaminothiazol-5-yl, 2-benzylaminothiazol-5-yl, 2-pyrrolidinothiazol-5-yl, 2-morpholinothiazol-5-yl, 4-methyl-2-dimethylaminothiazol-5-yl, 4-phenyl-2-benzylaminothiazol-5-yl or 4-chloro-2-piperidinothiazol-5-yl.

In formula I, $R^4$ is, for example, hydroxyl, methoxy, ethoxy, propoxy, isopropoxy, sec-butoxy or pentyloxy; phenoxy which is unsubstituted or substituted by $C_1-C_4$-alkyl, $C_1-C_4$-alkoxy or halogen, such as 2-methylphenoxy, 4-methylphenoxy, 3-methoxyphenoxy or 4-chlorophenoxy; phenylsulfonyl which is unsubstituted or substituted by $C_1-C_4$-alkyl or halogen, such as 4-methylphenylsulfonyl or 4-chlorophenylsulfonyl; pyrrolidino, piperidino or morpholino.

In formula I, $R^4$ may furthermore be a radical of a CH-acidic compound, for example 2-(pyrrolidino, piperidino or morpholino)-cyclopent-1-en-1-yl or -cyclohex-1-en-1-yl; cyclohexane-1,3-dion-2-yl which is unsubstituted or monosubstituted or disubstituted in ring position 5 by $C_1-C_4$-alkyl, such as cyclohexane-1,3-dion-2-yl, 5-methylcyclohexane-1,3-dion-2-yl, 5-ethylcyclohexane-;b 1,3-dion-2-yl or 5,5-dimethylcyclohexane-1,3-dion-2-yl; benzoylmethyl; cyano; nitromethyl; 2,4,6-trihydroxypyrimid-5-yl; 1-phenyl-3-methylpyrazol-5-on-4-yl; 5-hydroxy-3,4-dichlorfuran-2-yloxy; or a radical

where Y and Z are identical or different and independently of one another are each acetyl, benzoyl, $C_1-C_5$- alkoxycarbonyl or cyano, and, where Y is cyano, Z may furthermore be methyl, eg. bis-(acetyl-methyl, bis-(benzoyl)-methyl, bis-(methoxycarbonyl)-methyl, bis-(ethoxycarbonyl)-methyl, bis-(cyano)-methyl, acetyl-benzoyl-methyl, acetyl-methoxycarbonyl-methyl, benzoyl-ethoxycarbonyl-methyl, cyano-methoxycarbonyl-methyl or 1-cyanoeth-1-yl.

In formula I, the ring A may be substituted, for example, in ring position 6 or 8 by chlorine or bromine or in ring position 6 and 8 by chlorine. It may furthermore be substituted in ring position 7 by, for example, methyl, ethyl, propyl, isopropyl, butyl, hydroxyl, methoxy, ethoxy, isopropoxy, methylamino, ethylamino, propylamino, isopropylamino, butylamino, benzylamino, 2-chloroethylamino, dimethylamino, diethylamino, dibutylamino, dibenzylamino, methylethylamino, pyrrolidino, piperidino or morpholino. It may also be benzofused, for example as follows:

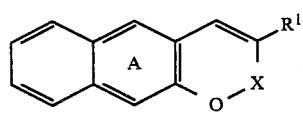,

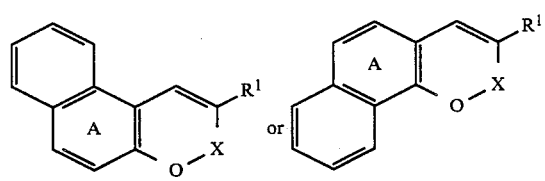

Preferred benzopyrans of the formula I are those in which $R^1$ is $C_1$–$C_5$-alkyl, $R^2$ is hydrogen, $R^3$ is carbazol-3-yl or unsubstituted or substituted phenyl and $R^4$ is a radical

The novel benzopyrans are advantageously obtained if a benzopyrylium compound of the formula II

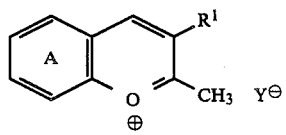   (II)

where $R^1$ and the ring A have the above meanings and $Y^\ominus$ is an anion, is reacted with an aldehyde of the formula III

   (III)

where $R^3$ has the above meanings, in a molar ratio of from 1:0.8 to 1:1.2, in the presence of an inert solvent at from 20° to 120° C., preferably from 40° to 80° C., and, in a subsequent stage, the resulting dye salt of the formula IV

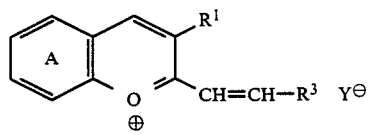   (IV)

where $R^1$, $R^3$, $Y^\ominus$ and the ring A have the above meanings, is reacted with a compound of the formula V

   (V)

where $R^4$ has the above meanings, in a molar ratio of from 1:1.1 to 1:2, in the presence of an inert solvent and of a base at from 20° to 120° C., preferably from 40° to 80° C.

Examples of suitable anions $Y^\ominus$ are trichlorozincate, tetrachloroferrate(III), bisulfate, nitrate or halide, such as chloride or bromide. Trichlorozincate and tetrachloroferrate (III) are particularly preferred.

Examples of advantageously inert solvents are methanol, ethanol, propanol, isopropanol, butanol and isobutanol. Mixtures of these alcohols with aromatic hydrocarbons, such as toluene or xylene, may also be used as the reaction medium.

Examples of suitable bases for the reaction of the dye salt IV with the compound V are alkali metal and alkaline earth metal carbonates, such as sodium carbonate, potassium carbonate, magnesium carbonate or calcium carbonate, alkaline earth metal oxides, such as magnesium oxide or calcium oxide, and alkali metal alkanolates, such as sodium or potassium methylate, ethylate or butylate. In general, from 1 to 3 moles of base are added per mole of dye salt.

The benzopyrylium salts II, aldehydes III and compounds IV which are required for the novel process are known.

The benzopyrans according to the invention are pale or colorless compounds whose solutions in inert organic solvents, in contact with electron acceptors, give dyeings in yellow, orange, red or blue hues, depending on the substitution of the benzopyran. Examples of electron acceptors are carboxylic acids, mineral acids, kaolin, bentonite, activated clay, aluminum silicate, attapulgite or any clay, acidic polymeric materials, such as condensates based on phenol (and/or phenolsulfonic acids) and formaldehyde, as well as metal oxides or salts, such as zinc oxide, alumina, zinc chloride, iron stearate and cobalt naphthenate.

Because of these propertiesm, the novel compounds of the formula I are useful as dye precursors in pressure-sensitive and heat-sensitive recording materials.

For use in pressure-sensitive systems the novel benzopyrans are advantageously enclosed in microcapsules, in the form of solutions in organic solvents, eg. chloroparaffins, partially hydrogenated di- or terphenyl, alkylbenzenes, alkylnaphthalenes, alkylated dibenzylbenzenes, liquid paraffin, mineral oil or conventional lower-boiling solvents, such as xylene or toluene, and the carrier, eg. paper, is coated with these microcapsules. When the microcapsules are subjected to pressure and are in contact with electron acceptors, dye formation then takes place at the pressure point.

Suitable processes for the preparation of microcapsules are disclosed in, for example, U.S.-A-2 800, 457, U.S.-A-2 800,458, DE-A-2 119 933 and EP-A-26 914. It is also possible for the novel compounds to be finely dispersed in wax or oil/wax mixtures by the method described in U.S.-A-3 103,404, and carriers, such as films or paper, to be coated with these mixtures. The resulting pressure-sensitive materials are suitable for copying onto papers coated with electron acceptors, and can be removed after use, like carbon paper.

The novel benzopyrans can also be used as dye precursors in heat-sensitive recording materials which contain a binder, a dye precursor and an electron acceptor on a carrier. The structure of such heat-sensitive recording materials and the composition of the layers which produce the color under the effective heat are known (for example, DE-A-2 228 581 and DE-A-2 110 854), as are the processes and apparatuses which are used to produce the dye.

The examples which follow illustrate the invention.

EXAMPLE 1

(a) Synthesis of the Dye Salt 331 g (1 mole) of 2,3-dimethylbenzopyrylium trichlorozincate and 149 g (1 mole) of 4-dimethylaminobenzaldehyde in 1,500 ml of methanol were refluxed for 4.5 hours. After the mixture had cooled, the precipitated dye was filtered off under suction and washed with methanol.

Yield: 400 g (86.6% of theory). mp.: 242°–244° C.

The dye salt of the formula

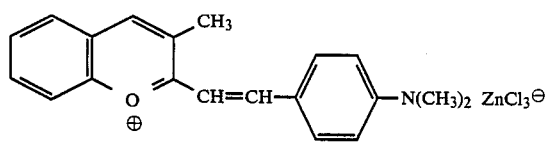

is obtained.

(b) Synthesis of the Dye Precursor 46 g (0.1 mole) of the dye salt prepared under (a) and 20 g of benzoylacetone (0.13 mole) in 500 ml of methanol were stirred in the presence of 22 g (0.2 mole) of sodium carbonate at 45° C. The reaction mixture was then added to a mixture of 1,600 ml of toluene and 1,600 ml of water. The organic phase was separated off, treated with active carbon and filtered, and the filtrate was evaporated down. 500 ml of methanol were added, and the precipitate which formed was then filtered off under suction, washed with 200 ml of methanol and dried at 60° C. under reduced pressure.

Yield: 34 g (76%). mp.: 165°–167° C.

A dye precursor of the formula

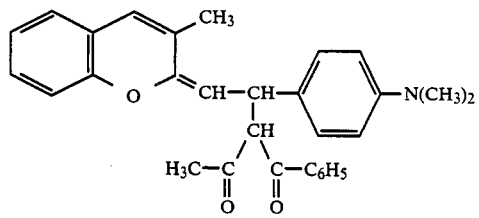

was obtained.

The components of the formula

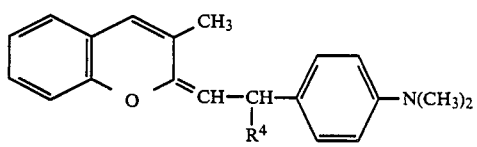

which are listed in Table 1 can be obtained in a similar manner.

TABLE 1

| Example | R⁴ | Mp. [°C.] | Color or $\lambda_{max}$ [nm] |
|---|---|---|---|
| 2 | —SO₂—⌬—CH₃ | 270–272 | blue |
| 3 | —CH(CO—C₆H₅)₂ | 193–195 | 628.9 |
| 4 | —CH(CN)₂ | 194–196 | 628.9 |
| 5 | —CH₂—NO₂ | 156–158 | blue |

EXAMPLE 6

(a) Synthesis of the Dye Salt 331 g (1 mole) of 2,3-dimethylbenzopyrylium trichlorozincate and 223 g (1 mole) of N-ethylcarbazole-3-aldehyde in 2,600 ml of methanol saturated with HCl are refluxed for 3 hours. After the mixture had cooled, the precipitated dye was filtered off under suction and washed with methanol.

Yield: 453 g (84.6% of theory). mp.: 240°–242° C.

A dye salt of the formula

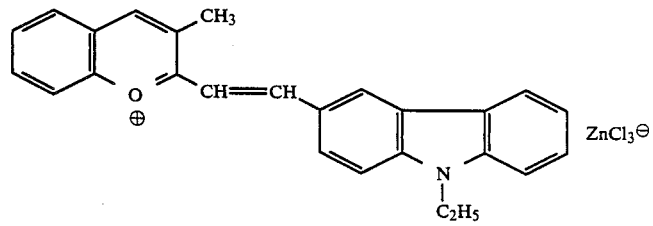

was obtained.

(b) Synthesis of the Dye Precursor 16 g (0.03 mole) of the dye salt prepared under (a) and 5 g (0.038 mole) of ethyl acetoacetate in 250 ml of methanol were stirred in the presence of 7 g (0.066 mole) of sodium carbonate at 45° C. The reaction mixture was then added to a mixture of 500 ml of toluene and 500 ml of water. The organic phase was separated off, treated with active carbon and filtered, and the filtrate was evaporated down. After the addition of 250 ml of methanol, the precipitate formed was filtered off under suction, washed with 70 ml of methanol and dried at 60° C. under reduced pressure.

Yield: 10 g (67.6% of theory. mp.: 132°–134° C.

A dye precursor of the formula

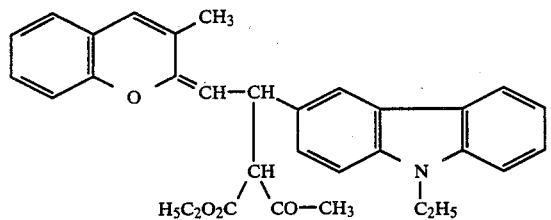

was obtained.

The components of the formula

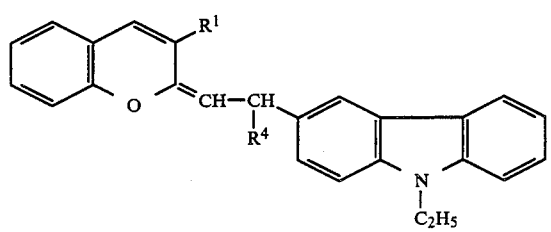

which are listed in Table 2 can be obtained in a similar manner.

TABLE 2

| Example | R⁴ | Mp. [°C.] | Color or λ_max [nm] |
|---|---|---|---|
| 7 | —SO₂—⌬—CH₃ | 156–158 | blue |
| 8 | —CH(CO—CH₃)₂ | 147–149 | 607.4 |
| 9 | —CH(CO—CH₃)(CO—C₆H₅) | 126–128 | 606.9 |
| 10 | —OH | 154–157 | 606.4 |
| 11 | —CH(CO—OC₂H₅)₂ | 182–184 | pale blue |
| 12 | —CH(CO—C₆H₅)₂ | 142–144 | 606.9 |
| 13 | —CH(CN)₂ | 241–243 | 607.4 |
| 14 | —CH(CN)(CO₂C₂H₅) | 193–195 | 607.9 |
| 15 | —O—⌬ | 187–189 | 607.9 |
| 16 | —CH₂—NO₂ | 154–156 | 605.4 |
| 17 | —CH(CO—OCH₃)₂ | | |

The dye precursors of the formula

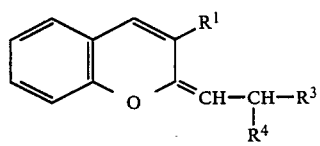

which are listed in Table 3 can be obtained similarly to Examples 1 to 6.

TABLE 3

| Example | R¹ | R³ | R⁴ | Mp. [°C.] | Color or λ_max [nm] |
|---|---|---|---|---|---|
| 18 | —CH₃ | —⌬—N(CH₂—C₆H₅)₂ | —SO₂—⌬—CH₃ | 146–148 | blue |
| 19 | —CH₃ | —⌬—N(CH₂—C₆H₅)₂ | —CH(CO—CH₃)₂ | 142–144 | pale lime green |
| 20 | —CH₃ | —⌬—N(CH₂—C₆H₅)₂ | —CH(CO—C₆H₅)₂ | 144–146 | 642.4 |
| 21 | —CH₃ | —⌬—N⌬O | —SO₂—⌬—CH₃ | 203–205 | blue |
| 21 | —CH₃ | —⌬—N⌬O | —SO₂—⌬—CH₃ | 203–205 | blue |

TABLE 3-continued
| Example | R¹ | R³ | R⁴ | Mp. [°C.] | Color or $\lambda_{max}$ [nm] |
|---|---|---|---|---|---|
| 22 | —CH₃ | 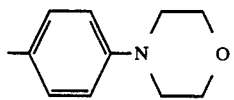 | —CH(CO—CH₃)₂ | 170–172 | blue |
| 23 | —CH₃ | 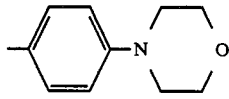 | 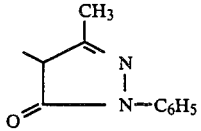 | 144–148 | green |
| 24 | —CH₃ | 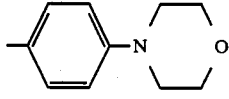 | —CH(CO—C₆H₅)₂ | 189 | 632.4 |
| 25 | —CH₃ | 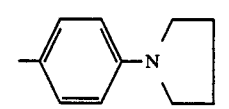 | 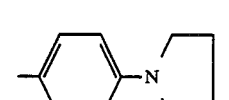 | 184–186 | blue |
| 26 | —CH₃ | 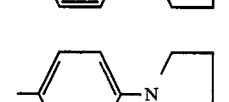 | 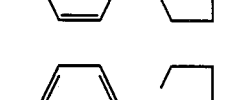 | oil | 672.9/631.4 |
| 27 | —CH₃ | 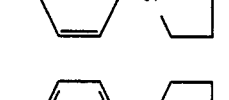 | 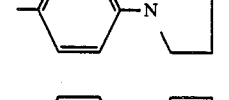 | 128–130 | 671.9/630.9 |
| 28 | —CH₃ | 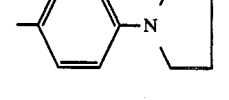 | —CH(CO—C₆H₅)₂ | 132–134 | 672.9/630.4 |
| 29 | —CH₃ | 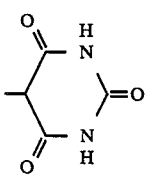 | —CH(CN)₂ | 203–205 | blue |
| 30 | —CH₃ | 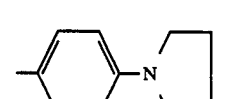 | 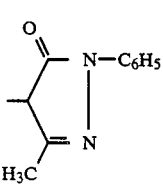 | oil | blue |
| 31 | —CH₃ | | | oil | blue |
| 32 | —CH₃ | | 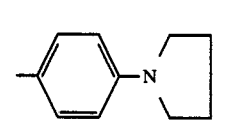 | 154–156 | blue |
| 33 | —CH₃ | | —OH | 195 | blue |

TABLE 3-continued

| Example | R¹ | R³ | R⁴ | Mp. [°C.] | Color or $\lambda_{max}$ [nm] |
|---|---|---|---|---|---|
| 34 | —CH₃ | 4-(piperidin-1-yl)phenyl | —CH(CO—C₆H₅)₂ | 178–180 | 519.3 |
| 35 | —CH₃ | 4-(piperidin-1-yl)phenyl | —CH(CO—CH₃)₂ | | |
| 36 | —CH₃ | 4-(piperidin-1-yl)phenyl | —CH(CO—CH₃)(CO—C₆H₅) | | |
| 37 | —CH₃ | 4-hydroxyphenyl | —CH(CO—CH₃)₂ | 165 | reddish violet |
| 38 | —CH₃ | 4-hydroxyphenyl | —CH(CO—CH₃)(CO—C₆H₅) | | reddish violet |
| 39 | —CH₃ | 4-methoxyphenyl | —CH(CO—CH₃)₂ | 98–102 | 523.8 |
| 40 | —CH₃ | 4-methoxyphenyl | —CH(CO—CH₃)(CO—C₆H₅) | 159–160 | reddish violet |
| 41 | —CH₃ | 4-methoxyphenyl | —OH | 136–140 | pale red |
| 42 | —CH₃ | 3,4-dimethoxyphenyl | —CH(CO—CH₃)(CO—C₆H₅) | oil | 542.8 |
| 43 | —CH₃ | 3,4-dimethoxyphenyl | —OH | 120–124 | reddish violet |
| 44 | —CH₃ | 3,4-dimethoxyphenyl | —CH(CO—CH₃)₂ | | violet |
| 45 | —CH₃ | 3,4-dimethoxyphenyl | —OH | 210–216 | violet |

TABLE 3-continued

| Example | R¹ | R³ | R⁴ | Mp. [°C.] | Color or $\lambda_{max}$ [nm] |
|---|---|---|---|---|---|
| 46 | —CH₃ | 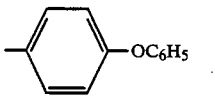 4-OC₆H₅-phenyl | —CH(CO—CH₃)₂ | 141-145 | pink |
| 47 | —CH₃ | 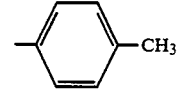 4-CH₃-phenyl | —CH(CO—CH₃)₂ | oil | orange |
| 48 | —CH₃ | 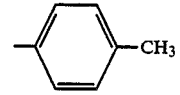 4-CH₃-phenyl | —OH | oil | orange |
| 49 | —CH₃ | 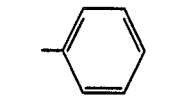 phenyl | —CH(CO—CH₃)₂ | 118 | yellow |
| 50 | —CH₃ | 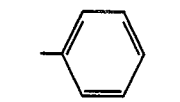 phenyl | —CH(CO—CH₃)(CO—C₆H₅) | 155 | yellow |
| 51 | —CH₃ | 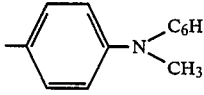 4-N(C₆H₅)(CH₃)-phenyl | —CH(CO—C₆H₅)(CO—CH₃) | 163-168 | 647.9 |
| 52 | —CH₃ | 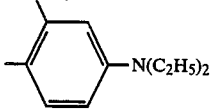 2-OCH₃-4-N(C₂H₅)₂-phenyl | —CH(CO—CH₃)₂ | oil | blue |
| 53 | —CH₃ | 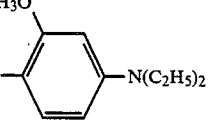 3-OCH₃-4-N(C₂H₅)₂-phenyl | —CH(CO—CH₃)(CO—C₆H₅) | oil | blue |
| 54 | —CH₃ | 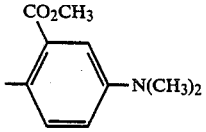 2-CO₂CH₃-4-N(CH₃)₂-phenyl | —SO₂-(4-CH₃-phenyl) | 181-183 | blue |
| 55 | —CH₃ | 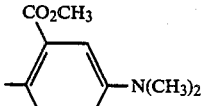 2-CO₂CH₃-4-N(CH₃)₂-phenyl | —CH(CO—CH₃)₂ | 130-132 | blue |
| 56 | —CH₃ | 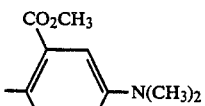 2-CO₂CH₃-4-N(CH₃)₂-phenyl | —CH(CO—C₂H₅)₂ | 166-168 | 644.9 |
| 57 | —CH₃ | 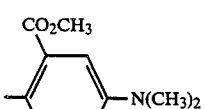 2-CO₂CH₃-4-N(CH₃)₂-phenyl | —CH(CN)₂ | 221-223 | 643.9 |

TABLE 3-continued

| Example | R¹ | R³ | R⁴ | Mp. [°C.] | Color or λ$_{max}$ [nm] |
|---|---|---|---|---|---|
| 58 | —CH₃ | 3-methylindole | —CH(CO—CH₃)₂ | 198–200 | 573.3 |
| 59 | —CH₃ | 3-methylindole | —CH(CN)(CO—OC₂H₅) | 134–137 | violet |
| 60 | —CH₃ | 3-methylindole | —CH(CN)₂ | | blue |
| 61 | —CH₃ | 2,3-dimethylindole | —CH(CO—C₆H₅)(CO—CH₃) | 204–207 | violet 549.3/583.8 |
| 62 | —CH₃ | 4-methyl-2-(N,N-diethylamino)thiazole | —CH(CO—C₆H₅)(CO—CH₃) | oil | blue |
| 63 | —CH₃ | 4-methyl-2-(N-methyl-N-phenylamino)thiazole | —CH(CO—C₆H₅)(CO—CH₃) | oil | blue |
| 64 | —CH₃ | 4-methyl-5-phenyl-2-(N,N-diethylamino)thiazole | —CH(CO—C₆H₅)(CO—CH₃) | oil | blue |
| 65 | —CH₃ | 1-naphthyl | —OH | 215 | violet |
| 66 | —C₂H₅ | 4-(N,N-dimethylamino)phenyl | —SO₂—C₆H₄—CH₃ | 148–150 | blue |
| 67 | —C₂H₅ | 4-(N,N-dimethylamino)phenyl | —CH(CO—CH₃)₂ | 128–130 | blue |
| 68 | —C₂H₅ | 4-(N,N-dimethylamino)-2-(CO₂CH₃)phenyl | —SO₂—C₆H₄—CH₃ | 166–168 | blue |

TABLE 3-continued

| Example | R¹ | R³ | R⁴ | Mp. [°C.] | Color or $\lambda_{max}$ [nm] |
|---|---|---|---|---|---|
| 69 | —C₂H₅ | 4-methyl-3-(CO₂CH₃)-phenyl-N(CH₃)₂ | —CH(CO—CH₃)₂ | 131–135 | blue |
| 70 | —CH(CH₃)₂ | 4-methyl-phenyl-N(CH₃)₂ | —SO₂—C₆H₄—CH₃ | 157–159 | blue |
| 71 | —CH(CH₃)₂ | 4-methyl-phenyl-N(CH₃)₂ | —CH(CO—CH₃)₂ | 133–135 | blue |
| 72 | —CH(CH₃)₂ | 4-methyl-phenyl-N(CH₃)₂ | —CH(CO—CH₃)(CO—C₆H₅) | 153–155 | 633.4 |
| 73 | —CH(CH₃)₂ | 4-methyl-phenyl-N(CH₃)₂ | —CH(CN)₂ | 195–197 | 633.4 |
| 74 | —CH(CH₃)₂ | 4-methyl-3-(CO₂CH₃)-phenyl-N(CH₃)₂ | —SO₂—C₆H₄—CH₃ | 129–131 | sky blue |
| 75 | —CH(CH₃)₂ | 4-methyl-3-(CO₂CH₃)-phenyl-N(CH₃)₂ | —CH(CO—CH₃)₂ | 148–150 | sky blue |
| 76 | —CH(CH₃)₂ | N-ethyl-methylcarbazolyl | —CH(CO—CH₃)₂ | 164–168 | blue |
| 77 | —CH(CH₃)₂ | N-ethyl-methylcarbazolyl | —CH(CO—C₆H₅)(CO—CH₃) | 118–120 | 605.4 |
| 78 | —CH(CH₃)₂ | N-ethyl-methylcarbazolyl | —CH(CO—C₆H₅)₂ | 143–145 | 606.4 |
| 79 | —CH(CH₃)₂ | N-ethyl-methylcarbazolyl | 2-methyl-1-morpholinocyclohexenyl | 141–143 | pale blue |

TABLE 3-continued

| Example | R¹ | R³ | R⁴ | Mp. [°C.] | Color or $\lambda_{max}$ [nm] |
|---|---|---|---|---|---|
| 80 | —CH₂—CH(CH₃)₂ | —C₆H₄—N(CH₃)₂ | —SO₂—C₆H₄—CH₃ | 140–142 | blue |
| 81 | —CH₂—CH(CH₃)₂ | —C₆H₄—N(CH₃)₂ | —CH(CO—CH₃)₂ | oil | blue |
| 82 | —CH₂—CH(CH₃)₂ | —C₆H₃(CO₂CH₃)—N(CH₃)₂ | —SO₂—C₆H₄—CH₃ | 163–165 | pale blue |
| 83 | —CH₂—CH(CH₃)₂ | —C₆H₃(CO₂CH₃)—N(CH₃)₂ | —CH(CO—CH₃)₂ | oil | greenish blue |
| 84 | —CH₂—CH(CH₃)₂ | —C₆H₃(OCH₃)—N(CH₂—C₆H₅)₂ | —CH(CO—CH₃)₂ | oil | blue to bluish green |
| 85 | —C₆H₅ | —C₆H₄—N(CH₃)₂ | —CH(CO—CH₃)₂ | oil | blue |
| 86 | —C₆H₅ | —C₆H₄—N(CH₃)₂ | —CH(CO—C₆H₅)(CO—CH₃) | oil | blue |
| 87 | —C₆H₅ | —C₆H₄—N(morpholino) | —CH(CO—CH₃)₂ | oil | blue |
| 88 | —C₆H₅ | —C₆H₄—N(morpholino) | —CH(CO—C₆H₅)(CO—CH₃) | oil | blue |
| 89 | —C₆H₅ | —C₆H₃(CO₂CH₃)—N(CH₃)₂ | —SO₂—C₆H₄—CH₃ | 179–181 | greenish blue |
| 90 | —C₆H₅ | —C₆H₃(CO₂CH₃)—N(CH₃)₂ | —CH(CO—CH₃)₂ | oil | greenish blue |

TABLE 3-continued

| Example | R¹ | R³ | R⁴ | Mp. [°C.] | Color or $\lambda_{max}$ [nm] |
|---|---|---|---|---|---|
| 91 | phenyl | 4-methyl-3-CO₂CH₃-6-N(CH₃)₂-phenyl | —OCH₃ | | greenish blue |
| 92 | phenyl | 4-methyl-3-CO₂CH₃-6-N(CH₃)₂-phenyl | morpholino (—N(CH₂CH₂)₂O) | oil | greenish blue |
| 93 | phenyl | H₅C₆–C(=C(CH₃)–S–)–N=C–N(C₂H₅)₂ (thiazoline) | —SO₂—C₆H₄—CH₃ | 180–182 | blue |
| 94 | —CH₂—C₆H₅ | 4-N(CH₃)₂-phenyl | —SO₂—C₆H₄—CH₃ | 198–200 | blue |
| 95 | —CH₂—C₆H₅ | 4-N(CH₃)₂-phenyl | —CH(CO—CH₃)₂ | 162–164 | blue |
| 96 | —OCH₃ | 4-N(CH₃)₂-phenyl | —SO₂—C₆H₄—CH₃ | 182 | blue |
| 97 | —OCH₃ | 4-N(CH₃)₂-phenyl | —CH(CO—CH₃)₂ | 168–170 | blue |
| 98 | —OCH₃ | 4-methyl-3-CO₂CH₃-6-N(CH₃)₂-phenyl | —SO₂—C₆H₄—CH₃ | 100–112 | blue |
| 99 | —OCH₃ | 4-methyl-3-CO₂CH₃-6-N(CH₃)₂-phenyl | —CH(CO—CH₃)₂ | oil | blue |
| 100 | —OCH₃ | 3-methyl-9-ethyl-carbazol-6-yl | —CH(CO—CH₃)₂ | 183–185 | blue |

EXAMPLE 101

The following dye precursor was obtained similarly to Example 1:

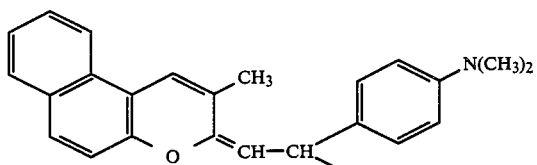

Mp.: 183–185° C.

EXAMPLE 102

(a) Synthesis of the Dye Salt 24 g (0.1 mole) of bis-(4-formylphenyl)-methylamine and 66 g (0.2 mole) of 2,3-dimethylbenzopyrylium trichlorozincate in 200 ml of methanol were refluxed for 3 hours, 200 ml of methylglycol were added and refluxing was then continued for a further ½ hour. The mixture was cooled, and the solvent was then separated off from the precipitated dye.

Yield: 66 g. mp.: 110° C.

(b) Synthesis of the Dye Precursor 26 g (0.03 mole) of the dye salt prepared under (a) and 8 g (0.08 mole) of acetylacetone were heated at 50° C. for 3 hours in the presence of 14 g (0.13 mole) of sodium carbonate in a mixture of 200 ml of methanol and 100 ml of toluene. The reaction mixture was then added to a mixture of 500 ml of toluene and 500 ml of water. The organic phase was separated off, treated with active carbon and filtered, and the filtrate was evaporated down. The residue was added dropwise to ice-cooled methanol, and the precipitate formed was filtered off under suction at 0° C.

Yield: 7 g. mp.: 166°–168° C.

A dye precursor of the formula

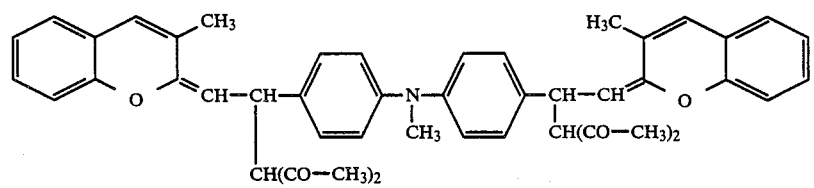

was obtained.

EXAMPLE 103

The dye salt prepared in Example 102a was used and the following dye precursor was obtained by a method similar to that described in Example 102b:

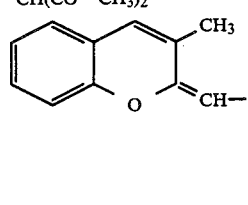

EXAMPLE 104

(a) Synthesis of the Dye Salt 66 g (0.2 mole) of 2,3-dimethylbenzopyrylium trichlorozincate and 33 g (0.1 mole) of ethylenebis-[N-ethyl-N-(4-formylphenyl)]-amine in 400 ml of methanol were refluxed for 4 hours. After the mixture had cooled, the precipitated dye was filtered off under suction and washed with methanol.

Yield: 82 g. mp.: 255°–260° C.

(b) Synthesis of the Dye Precursor 28.5 g (0.03 mole) of the dye salt prepared under (a) and 13 g (0.08 mole) of benzoylacetone were stirred under reflux for 7 hours in the presence of 15 g (0.14 mole) of sodium carbonate in a mixture of 350 ml of methanol and 100 ml of toluene. The reaction mixture was then added to a mixture of 500 ml of toluene and 500 ml of water. The organic phase was separated off, treated with active carbon and filtered, and the filtrate was evaporated down. The residue was diluted with methylglycol, and methanol was added. The precipitate formed was filtered off under suction, washed with methanol and dried at 60° C. under reduced pressure.

Yield: 7 g. mp.: 132°–140° C.

A dye precursor of the formula

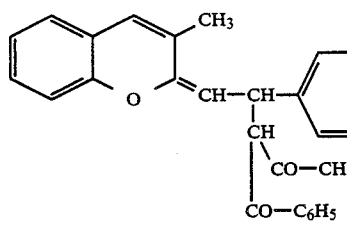 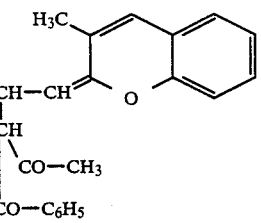

was obtained.

EXAMPLE 105

(a) Synthesis of the Dye Salt 21.9 g (0.05 mole) of 2-cyclohexylidene-2,3,4,5-tetrahydroxanthylium trichlorozincate and 7.2 g (0.05 mole) of indoline-3-carbaldehyde in 320 ml of n-butanol were refluxed for one hour. The dye precipitated after the mixture had been cooled was filtered off under suction.

Yield: 21 g. mp.: 243°–245° C.

A dye salt of the formula

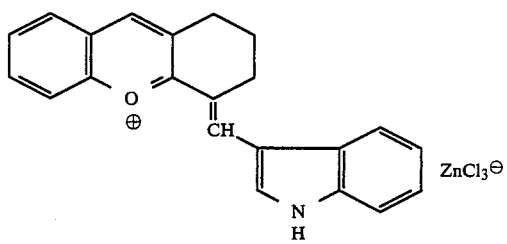

was obtained.

(b) Synthesis of the Dye Precursor 9.7 g (0.02 mole) of the dye salt prepared under (a) and 2.7 g (0.027 mole) of acetylacetone in 100 ml of methanol were stirred in the presence of 4.7 g (0.044 mole) of sodium carbonate for 4 hours at 45° C. The reaction mixture was then added to a mixture of 300 ml of toluene and 300 ml of water. The organic phase was separated off, treated with active carbon and filtered, and the filtrate was evaporated down. After the addition of 100 ml of methanol, the precipitate formed was filtered off under suction, washed with 40 ml of methanol and dried at 60° C. under reduced pressure.

Yield: 5 g. mp.: 162°–170° C.

A dye precursor of the formula

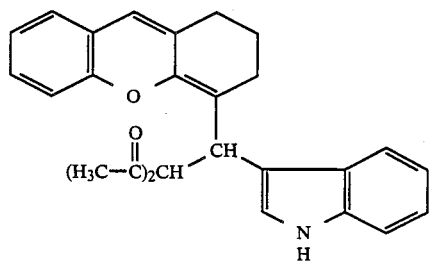

was obtained.

We claim:
1. A benzopyran of the formula I

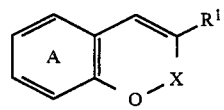 (I)

where $R^1$ is unsubstituted $C_1$–$C_8$-alkyl, unsubstituted or substituted phenyl, $C_1$–$C_5$-alkoxy or halogen, X is a radical $$\diagup C=C-CH-R^3 \atop \phantom{C=}R^2 \phantom{CH}R^4$$

$R^2$ is hydrogen or, together with $R^1$, is $C_2$—$R^3$ is carbazol-3-yl or 1,2,3,4,4a,9a-hexahydrocarbazol-6-yl, each of which may be substituted on the nitrogen atom by $C_1$–$C_5$-alkyl or benzyl, and the ring A may be fused to a benzo ring, may be substituted by $C_1$–$C_4$-alkyl, chlorine or bromine, or may be substituted in ring position 7 by $C_1$–$C_5$-mono- or dialkylamino (each of which in turn may be substituted by chlorine or phenyl), pyrrolidino, piperidino, morpholino, hydroxyl or $C_1$–$C_4$-alkoxy.

* * * * *

UNITED STATES PATENT AND TRADEMARK OFFICE
CERTIFICATE OF CORRECTION

PATENT NO. : 4,841,050
DATED : June 20, 1989
INVENTOR(S) : ANDREAS GUENTNER, ET AL.

It is certified that error appears in the above-identified patent and that said Letters Patent is hereby corrected as shown below:

In Claim 1, line 7, delete "or, together with $R^1$, is $C_2$-".

Line 10, after "benzyl," insert --and $R^4$ is Y-CH-Z where Y and Z are identical or different and independently of one another are each acetyl, benzoyl, $C_1$-$C_5$ alkoxycarbonyl or cyano--.

Signed and Sealed this

Twenty-second Day of January, 1991

*Attest:*

HARRY F. MANBECK, JR.

*Attesting Officer*  *Commissioner of Patents and Trademarks*